United States Patent [19]

Brown

[11] 4,173,462
[45] Nov. 6, 1979

[54] PHENOXYBENZYLPHOSPHONIUM SALT HERBICIDES AND PLANT GROWTH REGULANTS

[75] Inventor: Michael J. Brown, Randolph Township, Morris County, N.J.

[73] Assignee: GAF Corporation, New York, N.Y.

[21] Appl. No.: 861,162

[22] Filed: Dec. 16, 1977

[51] Int. Cl.$^2$ .......................... A01N 9/36; A01N 5/00
[52] U.S. Cl. ............................................. 71/86; 71/76
[58] Field of Search ....................................... 71/86, 76

[56] References Cited
U.S. PATENT DOCUMENTS

| 3,103,431 | 9/1963 | Wilson, Jr. ........................ 71/86 |
| 3,230,069 | 1/1966 | Preston, Jr. ....................... 71/86 |
| 3,364,107 | 1/1968 | Berenson et al. .................. 71/86 |
| 3,804,950 | 4/1974 | Diamond ......................... 424/198 |
| 4,066,435 | 1/1978 | Howe ............................... 71/86 |

Primary Examiner—Catherine L. Mills
Attorney, Agent, or Firm—Walter C. Kehm

[57] ABSTRACT

The herbicides and plant growth regulants having the formula:

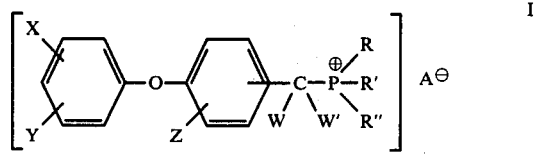

wherein $A^\ominus$ is a halogen anion; X, Y and Z are each independently hydrogen, a halogen atom or haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is hydogen, —CHO or —CHN(R''')$_2$ where each R''' is independently hydrogen or alkyl of from 1 to 4 carbon atoms, optionally substituted with halogen; and W' is hydrogen or represents a bond forming a double bond between C and W when W is —CHN(R''')$_2$. The invention also relates to the method of preparing said herbicidal and plant growth regulant compounds together with their formulations or compositions as agricultural products and agricultural use thereof.

21 Claims, No Drawings

PHENOXYBENZYLPHOSPHONIUM SALT HERBICIDES AND PLANT GROWTH REGULANTS

This application relates to a new class of herbicidal and plant growth regulant compounds, a process for their preparation and the application of said compounds, utilized either alone as an agricultural chemical or in chemical formulations with a carrier, as a liquid spray or dust. The compounds of this invention find utility as herbicides and plant growth regulators which are ecologically safe and leave no toxic residue in the plants or on the soil.

It is an object of this invention to provide new and useful herbicides and plant growth regulants which are not harmful to the environment.

Another object of the present invention is to provide herbicides having a high selectivity for weeds, while having substantially no detrimental effect on crops.

Another object of this invention is to provide a method for treatment and destruction of noxious weeds.

Still another object of this invention is to provide formulations for the present herbicides and plant growth regulants for use in agricultural applications as sprays or dusts.

These and other objects of the present invention will become apparent from the following description and disclosure.

According to this invention, there is provided phosphonium salt herbicides and plant gorwth regulants having the formula:

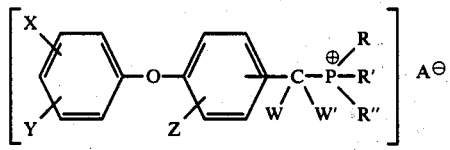

wherein $A^{\ominus}$ is a halogen anion; X, Y and Z are each independently hydrogen, a halogen atom or a haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is hydrogen, —CHO or —CHN(R''')$_2$ where each R''' is independently hydrogen or alkyl of from 1 to 4 carbon atoms, optionally substituted with halogen; and W' is hydrogen or represents a bond forming a double bond between C and W when W is —CHN(R''')$_2$. The halogen referred to in the above phosphonium salt compounds is fluorine, chlorine, bromine or iodine.

Of the above group of compounds, those wherein one of X or Y is hydrogen and the other is halogen or perhaloalkyl, W and W' are hydrogen, R, R' and R" are the same and are either lower alkyl or phenyl and $A^{\ominus}$ is a bromine or chlorine anion are preferred as herbicides and plant growth regulants in the present invention.

Most preferred as the herbicides and plant growth regulants of the present invention are those having the formula:

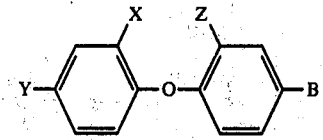

wherein X is hydrogen or chlorine; Y is hydrogen or trifluoromethyl; Z is hydrogen or, when x and Y are hydrogen, then Z is chlorine; and B is —CH$_2$P(R)$_3$ where R is ethyl, butyl or phenyl.

In general, the phenoxy benzyl phosphonium compounds of the present invention may be prepared according to the reaction illustrated by the following equation I, wherein the reactants in each stage are contacted in a mole ratio of between about 1:2 and about 2:1, preferably stochiometric amounts of the required reactants, and the various reactions are effected at a temperature between about 0° C. and about 180° C. under from about 5 to about 25 psig pressure, more desirably between about 5° C. and about 150° C. under atmospheric pressure. Stage (2) of the reaction is beneficially carried out in the presence of a peroxy type catalyst, e.g. benzoyl peroxide. Under most preferred conditions, reaction (3) is carried out at between about 10° C. and 35° C. under atmospheric pressure. The reaction, usually carried out over a period of from about 30 minutes to about 4 hours, is effected in liquid phase with an organic solvent; chloroform being illustrative of the solvents selected for stage (3) of the reaction with a phosphine. It is to be understood, however, that other solvents, such as xylene, toluene, bromoform, methyl isobutyl ketone, dichloromethane, carbontetrachloride, ethanol, propanol, dimethylformamide, 2-methoxyethyl ether, or other solvents conventionally employed for quaterinization reactions, may be substituted, in the whole or in part, for chloroform in stage (3) of the reaction illustrated by Equation I.

Since the product of stage (1) between a halogenated benzene and the metal oxide of a toluene and the product of stage (2) between a halogenated phenyl benzyl ether and N-bromosuccinimide are known, the novel stage in process of the present invention may be considered to reside in stage (3) where phenoxybenzylbromide or other halide such as the corresponding chloride or iodide, is reacted with a trisubstituted phosphine to provide the novel quaternized product.

Since the phenoxybenzyl halide reactants of stage (3) in Equation I are generally known in the art, alternative methods for the preparation of the correspondingly substituted phenoxy benzylphosphonium quaternized salts will become apparent to those skilled in the art from this disclosure. For example, free radical halogenation of the phenoxybenzyl product of stage (1) in the absence or presence of a catalyst such as a metal halide or UV light can be effected to produce the corresponding halomethyl analogue or reactant of stage (3).

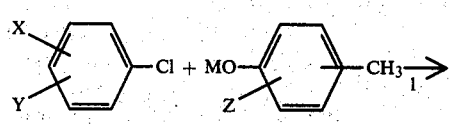

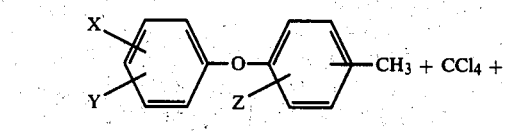

-continued

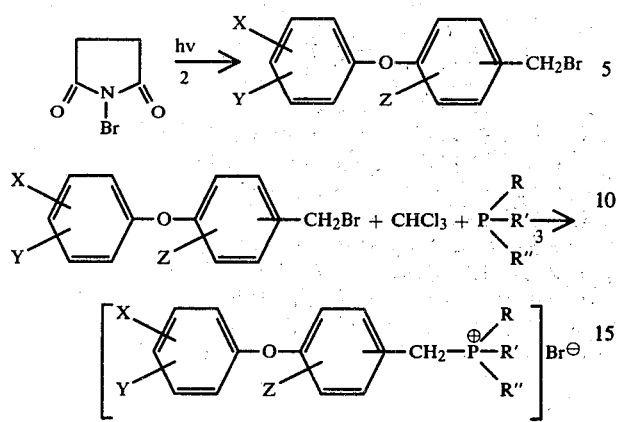

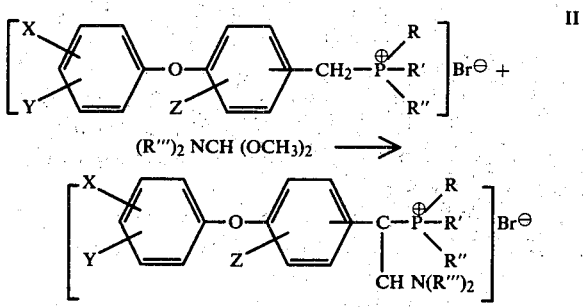

In the above reaction, M represents an alkali metal, such as Li, Na, K or Ca; Na or K being preferred, X, Y, Z, R, R' and R" have the meaning set forth above for Formula I. The product of stage 3 can be isolated and recovered by distilling off solvent and then triturating the product with petroleum ether, cyclohexane or other inert trituating agent. The corresponding chloride anion may be obtained from the final product of Equation I by a substitution reaction in which the bromine of the product reacts with an excess of sodium- or potassium-chloride in aqueous solution. The substitution reaction is effected under atmospheric pressure at a temperature of between about 5° C. and about 150° C. in the presence of chloroform or any other suitable water-immisible inert solvent.

The corresponding fluoride or iodide anions may be obtained from the product of Equation I by phase-transfer. Generally, to obtain the various halide anions of the present invention, the product of reaction (3) in Equation I is dissolved in chloroform or other suitable solvent, such as bromoform or any water-immisible inert solvent. To this solution an aqueous alkali metal halide or ammonium halide solution, wherein the halide of the alkali metal or ammonium salt is capable of replacing the bromine anion of the phosphonium compound, is added with agitation until two liquid layers are formed; usually within a period of from 15 minutes to 4 hours. The preferred alkali metal halides are the iodide or fluoride of sodium or potassium.

The phase-transfer reaction is carried out at a temperature between about 5° C. and about 125° C. preferably between about 10° C. and about 100° C., under atmospheric conditions. The substituted halide anion product is recovered by drawing off the lower liquid product phase or by decanting the upper liquid aqueous alkali metal halide or ammonium halide phase. The product is then isolated by evaporating the lower product phase to dryness, washing the product with water, followed by evaporation to dryness. The washing and drying operation can be repeated as desired.

To obtain the amino substituted phosphonium salt of the present invention, the final product of Equation I, or the corresponding chloride, fluoride, or iodide anion of the product of Equation I, is reacted with an aminodimethoxy-methane in an anhydrous alcoholic solution, e.g. an anhydrous solution of ethanol, propanol, butanol, pentanol, or another inert organic solvent. This reaction is carried out at a temperature of between about 10° C. and about 180° C. under from about 5 psig to about 30 psig, preferably at a temperature between about 80° C. and about 140° C. under atmospheric pressure. The following Equation II exemplifies such a viable process for the preparation of the amino substituted phosphonium compounds of the present invention using bromine anion for purposes of illustration.

In the above equations, X, Y, Z, R, R', R" and R'" have the meaning set forth in Formula I of the preceeding disclosure.

The above amino substituted product is recovered from the reaction mixture by evaporation to dryness to remove alcoholic by-product and trituration with petroleum ether, cyclohexane or any other inert agent conventionally employed for forming a fine particulate solid or powder.

To obtain the aldehyde derivative of the phosphonium salt of the present invention, the product of Equation II, or the corresponding fluoride, chloride or iodide anion of said product, is reacted with an aqueous solution of mineral acid such as a 2 to 50% solution of HCl, $H_2SO_4$, $HNO_3$, etc., at a temperature of between about 25° C. and about 100° C. under from about 5 psig to about 30 psig; preferably between about 50° C. and about 80° C. under atmospheric pressure. The corresponding aldehyde substituted phosphonium compound is formed within a period of from about 15 minutes to about 1.5 hours and is recovered from the reaction mixture by extraction with chloroform or another inert organic solvent conventionally employed for removing acid impurities. The solvent is then evaporated and the product triturated with a suitable agent, such as petroleum ether.

The following Equation III illustrates such a viable process for the preparation of the aldehyde derivative of the halogenated phenoxybenzyl phosphonium compound.

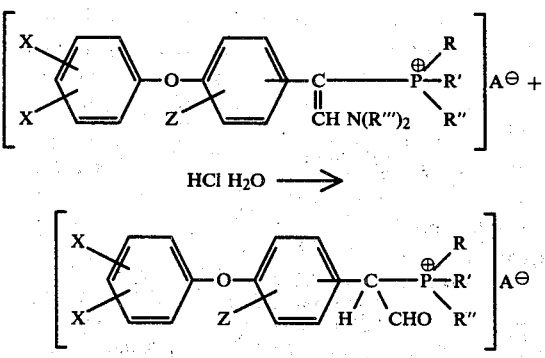

The product of Equation III may be converted into the corresponding dehydrohalogenated compound as shown in Equation IV. The conversion is effected by passing the aldehyde substituted phosphonium compound (e.g. the product of Equation III) downwardly through an anion exchange column (e.g. Amberlite CG-4B, 200-400 mesh) in an alcohol solution, e.g. a methanol solution, at ambient temperature. The product is then isolated by evaporation to dryness followed by trituration with cyclohexane or petroleum ether or any other conventional trituration liquid. As indicated, the product of Equation IV exists in equilibrium.

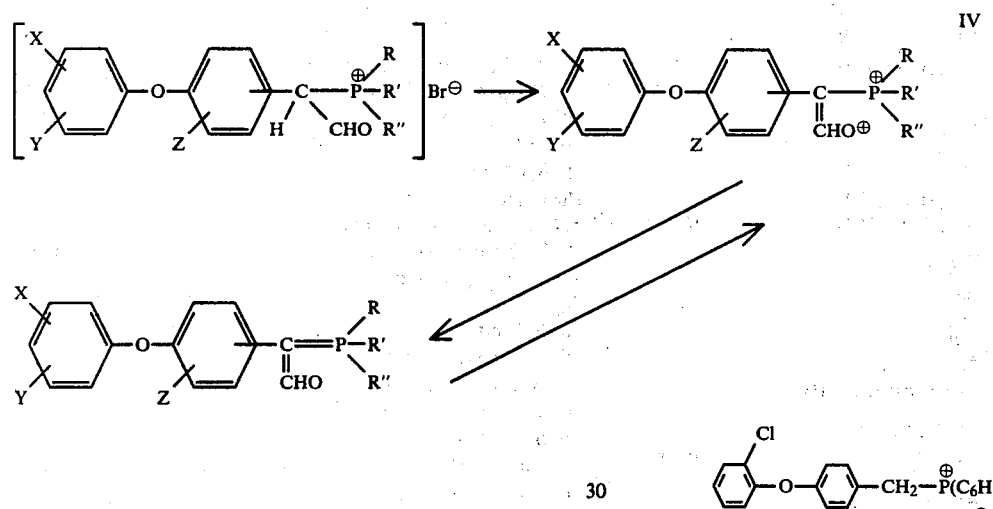

IV

The following compounds shown in Table I are representative of the novel compounds of the present invention.

TABLE I

| Compound Number | Structure | °C. Melt Pt. |
|---|---|---|
| 1 | 2-Cl-C₆H₄-O-C₆H₄-CH₂P(C₄H₉)₃⁺ Br⁻ (meta) | 145-7 |
| 2 | 2-Cl-C₆H₄-O-C₆H₄-CH₂P(C₄H₉)₃⁺ Br⁻ (para) | 115-9 |
| 3 | 4-CF₃-C₆H₄-O-C₆H₄-CH₂P(C₄H₉)₃⁺ Br⁻ (meta) | 88-90 |
| 4 | 4-CF₃-C₆H₄-O-C₆H₄-CH₂P(C₂H₅)₃⁺ Br⁻ (meta) | 144-6 |
| 5 | 2-Cl-C₆H₄-O-C₆H₄-CH₂P(C₂H₅)₃⁺ Br⁻ (ortho) | 144-6 |
| 6 | 2-Cl-C₆H₄-O-C₆H₄-CH₂P(C₂H₅)₃⁺ Br⁻ (para) | 119-21 |
| 7 | 2-Cl-C₆H₄-O-C₆H₄-CH₂P(C₂H₅)₃⁺ Br⁻ (meta) | 151-3 |
| 8 | 2-Cl-C₆H₄-O-C₆H₄-CH₂P(C₄H₉)₃⁺ Br⁻ (ortho) | 88-90 |
| 9 | 2-Cl-C₆H₄-O-C₆H₄-CH₂-P(C₆H₅)₃⁺ Br⁻ (para) | 243-50 |
| 10 | 2-Cl-C₆H₄-O-C₆H₄-CH₂P(C₆H₅)₃⁺ Br⁻ (ortho) | 105 |
| 11 | 4-CF₃-C₆H₄-O-C₆H₄-CH₂P(C₄H₉)₃⁺ Br⁻ (ortho) | 112-3 |
| 12 | 4-CF₃-C₆H₄-O-C₆H₄-CH₂P(C₂H₅)₃⁺ Br⁻ (ortho) | 152-5 |
| 13 | 4-CF₃-C₆H₄-O-C₆H₄-CH₂P(C₆H₅)₃⁺ Br⁻ (meta) | 145-9 |
| 14 | 2-Cl-C₆H₄-O-C₆H₄-CH₂P(C₆H₅)₃⁺ Br⁻ (meta) | 118-22 |
| 15 | 4-CF₃-C₆H₄-O-C₆H₄-CH₂P(C₆H₅)₃⁺ Br⁻ (ortho) | 91 |
| 16 | 4-CF₃-3-Cl-C₆H₃-O-2-Cl-C₆H₃-CH₂P(C₄H₉)₃⁺ Br⁻ | 90 |
| 17 | 4-CF₃-3-Cl-C₆H₃-O-2-Cl-C₆H₃-CH₂P(C₆H₅)₃⁺ Br⁻ | 100 |
| 18 | 4-CF₃-C₆H₄-O-2,3-Cl₂-C₆H₂-CH₂P(C₂H₅)₃⁺ Br⁻ | 134-7 |

TABLE I-continued

| Compound Number | Structure | °C. Melt Pt. |
|---|---|---|
| 19 | Cl-substituted diphenyl ether with $CH_2\overset{\oplus}{P}(C_4H_9)_3$ $Br^{\ominus}$ | 84–8 |
| 20 | Cl-substituted diphenyl ether with $CH_2\overset{\oplus}{P}(C_6H_5)_3$ $Br^{\ominus}$ | 74–8 |
| 21 | Cl-substituted diphenyl ether with $CH_2\overset{\oplus}{P}(C_2H_5)_3$ $Br^{\ominus}$ | <25 |
| 22 | Cl-substituted diphenyl ether with $CH_2\overset{\oplus}{P}(C_4H_9)_3$ $Cl^{\ominus}$ | 159–60 |
| 23 | Cl-substituted diphenyl ether with $C\!=\!=\!CH\,N(CH_3)_2$, $\overset{\oplus}{P}(C_6H_5)_3$ $Br^{\oplus}$ | 50–8 |
| 24 | Cl-substituted diphenyl ether with $CH\!-\!-\!CHO$, $\overset{\oplus}{P}(C_6H_5)_3$ $Br^{\ominus}$ | 184–8 |
| 25 | Cl-substituted diphenyl ether with $C\!=\!=\!CHO^{\ominus}$, $\overset{\oplus}{P}(C_6H_5)_3$ | 75 |

A. PREPARATION OF COMPOUNDS 1–21

Of the above compounds, 1–21 were prepared by reacting the corresponding halogenated phenyl tolyl ether with N-bromo-succinimide in the liquid phase where carbon tetrachloride is employed as the solvent. The reaction was carried out in a glass reactor with constant mixing and irradiation with ultraviolet light in the presence of a catalytic amount of benzoyl peroxide. After conversion was effected, the corresponding halogenated phenoxybromotoluene was recovered by filtering to remove the insoluble by-product, i.e. succinimide, and then distilling off the carbon tetrachloride. The desired intermediate product, i.e. brominated ether derivative, was then purified by vacuum distillation. The recovered intermediate product was then dissolved in chloroform or xylene and reacted with phosphine in a sealed glass reactor with constant stirring to obtain the product corresponding to the Compound Number shown in the following Table II. Other conditions of the reactions are also reported in Table II.

TABLE II

PREPARATION OF COMPOUNDS 1 THROUGH 21 LISTED IN TABLE I

| Compd. No. | gms of halogenated phenyl tolyl ether | reactn conds. temp.(°C.)/ press.(psig)/ time (hrs) | gms. N-bromo succinimide /mls. $CCl_4$ solvent | gms. halogenated phenoxy bromo- toluene deriv./ mls. solvent | gms of phosphine | reactn. conds. temp.(°C.)/ press.(psig)/ time (hrs) | Method of Recovery |
|---|---|---|---|---|---|---|---|
| 1. | 175g of Cl/CH₃ diphenyl ether | 77/atmospheric/24 | 185.1/500 | 29.7/50 xylene | 22.3g of $P(C_4H_9)_3$ | 25/atmospheric/2 | filtration followed by trituration with petroleum ether |
| 2. | 112g of Cl/CH₃ diphenyl ether | 77/atmospheric/28 | 118/700 | 10/100 xylene | 7.4g of $P(C_4H_9)_3$ | 138/atmospheric/8.5 | filtration followed by trituration with xylene and then petroleum ether |
| 3. | 26g of $F_3C$–/CH₃ diphenyl ether | 77/atmospheric/18 | 19.8/100 | 7/25 $CHCl_3$ | 4.2g of $P(C_4H_9)_3$ | 25/atmospheric/16 | evaporation to dryness followed by trituration with petroleum ether |
| 4. | 26g of $F_3C$–/CH₃ diphenyl ether | 77/atmospheric/18 | 19.8/100 | 5/25 $CHCl_3$ | 3g of $P(C_2H_5)_3$ | 25/atmospheric/20 | Same as #3 |
| | 80g of | | | | | | |

TABLE II-continued

PREPARATION OF COMPOUNDS 1 THROUGH 21 LISTED IN TABLE I

| Compd. No. | gms of halogenated phenyl tolyl ether | reactn. conds. temp.(°C.)/ press.(psig)/ time (hrs) | gms. N-bromo succinimide /mls. CCl₄ solvent | gms. halogenated phenoxy bromotoluene deriv./ mls. solvent | gms of phosphine | reactn. conds. temp.(°C.)/ press.(psig)/ time (hrs) | Method of Recovery |
|---|---|---|---|---|---|---|---|
| 5. | 112g of 2-chloro-phenyl 2-tolyl ether (Cl on phenyl, CH₃ ortho on tolyl) | 77/atmospheric/24 | 78.2/400 | 10/50 CHCl₃ | 4.4g of P(C₂H₅)₃ | 25/atmospheric/20 | Same as #3 |
| 6. | 112g of 2-chloro-phenyl 4-tolyl ether | 77/atmospheric/28 | 118/700 | 5/25 CHCl₃ | 2.2g of P(C₂H₅)₃ | 25/atmospheric/20 | Same as #3 |
| 7. | 175g of 2-chloro-phenyl 3-tolyl ether | 77/atmospheric/24 | 185.1/500 | 5/25 CHCl₃ | 2.2g of P(C₂H₅)₃ | 25/atmospheric/20 | Same as #3 |
| 8. | 80g of 2-chloro-phenyl 2-tolyl ether | 77/atmospheric/24 | 78.2/400 | 10/50 CHCl₃ | 7.6g of P(C₄H₉)₃ | 25/atmospheric/20 | Same as #3 |
| 9. | 112g of 2-chloro-phenyl 4-tolyl ether | 77/atmospheric/28 | 118/700 | 10/50 CHCl₃ | 10.3g of P(C₅H₆)₃ | 25/atmospheric/20 | Same as #3 |
| 10. | 80g of 2-chloro-phenyl 2-tolyl ether | 77/atmospheric/24 | 78.2/400 | 10/50 CHCl₃ | 10.3g of P(C₆H₅)₃ | 25/atmospheric/20 | Same as #3 |
| 11. | 51.23 of 4-trifluoromethyl-phenyl 2-tolyl ether | 77/atmospheric/22 | 41.6/200 | 10/50 CHCl₃ | 6.7g of P(C₄H₉)₃ | 25/atmospheric/20 | Same as #3 |
| 12. | 51.2 of 4-trifluoromethyl-phenyl 2-tolyl ether | 77/atmospheric/22 | 41.6/200 | 10/50 CHCl₃ | 3.9g of P(C₂H₅)₃ | 25/atmospheric/20 | Same as #3 |
| 13. | 26g of 4-trifluoromethyl-phenyl 3-tolyl ether | 77/atmospheric/18 | 19.8/100 | 10/50 CHCl₃ | 8.7g of P(C₆H₅)₃ | 25/atmospheric/20 | Same as #3 |
| 14. | 52g of 2-chloro-phenyl 3-tolyl ether | 77/atmospheric/24 | 185.1/500 | 10/50 CHCl₃ | 10.3g of P(C₆H₅)₃ | 25/atmospheric/20 | Same as #3 |
| 15. | 51.2g of 4-trifluoromethyl-phenyl 2-tolyl ether | 77/atmospheric/22 | 41.6/200 | 10/50 CHCl₃ | 8.7g of P(C₆H₅)₃ | 25/atmospheric/20 | Same as #3 |

64.8g of

TABLE II-continued
PREPARATION OF COMPOUNDS 1 THROUGH 21 LISTED IN TABLE I

| Compd. No. | gms of halogenated phenyl tolyl ether | reactn conds. temp.(°C.)/ press.(psig)/ time (hrs) | gms. N-bromo succinimide /mls. $CCl_4$ solvent | gms. halogenated phenoxy bromotoluene deriv./ mls. solvent | gms of phosphine | reactn. conds. temp.(°C.)/ press.(psig)/ time (hrs) | Method of Recovery |
|---|---|---|---|---|---|---|---|
| 16. | 64.8g of [F$_3$C—⌬(Cl)—O—⌬(Cl,CH$_3$)] | 77/atmospheric/48 | 39.5/200 | 10/50 $CHCl_3$ | 3.5g of $P(C_4H_9)_3$ | 25/atmospheric/20 | Same as #3 |
| 17. | 64.8g of [F$_3$C—⌬(Cl)—O—⌬(Cl,CH$_3$)] | 77/atmospheric/48 | 39.5/200 | 10/50 $CHCl_3$ | 4.7g of $P(C_6H_5)_3$ | 25/atmospheric/20 | Same as #3 |
| 18. | 66.8g of [F$_3$C—⌬(Cl)—O—⌬(Cl,CH$_3$)] | 77/atmospheric/48 | 39.5/200 | 10/50 $CHCl_3$ | 2.1g of $P(C_2H_5)_3$ | 25/atmospheric/20 | Same as #3 |
| 19. | 45.5g of [⌬—O—⌬(Cl,CH$_3$)] | 77/atmospheric/23 | 41/200 | 10/50 $CHCl_3$ | 7.5g of $P(C_4H_9)_3$ | 25/atmospheric/20 | Same as #3 |
| 20. | 45.5g of [⌬—O—⌬(Cl,CH$_3$)] | 77/atmospheric/23 | 41/200 | 6.5/50 $CHCl_3$ | 6.3g of $P(C_6H_5)_3$ | 25/atmospheric/20 | Same as #3 |
| 21. | 45.5g of [⌬—O—⌬(Cl,CH$_3$)] | 77/atmospheric/23 | 41/200 | 6.5/50 $CHCl_3$ | 2.8g of $P(C_2H_5)_3$ | 25/atmospheric/20 | Same as #3 |

B. PREPARATION OF COMPOUND 22

Compound 1 in the above Table I (5 g) was dissolved in 25 ml of chloroform and introduced into a reactor. To this solution was added a saturated solution of sodium chloride (100 ml) to form a 2 phase mixture and the resulting mixture was agitated at a temperature of 25° C. for 0.5 hour. The lower layer was drawn off, dried over anhydrous magnesium sulfate, filtered and evaporated to dryness to recover 4.2 g of 2-chlorophenoxy-3'-benzyltributylphosphonium chloride.

The corresponding chlorides of compounds 2 through 21 are prepared in a similar manner with concentrated aqueous solutions of potassium chloride or sodium chloride, e.g. saturated solutions by reacting at a temperature of from 25° C. to 100° C., e.g. 25° C. under atmospheric pressure and recovering the product as set forth above.

It is to be understood that the corresponding fluoride or iodide phosphonium salts of compounds 1 to 21 are similarly prepared by substituting saturated aqueous solutions of potassium fluoride or iodide or sodium fluoride or iodide in the above example.

C. PREPARATION OF COMPOUND 23

Compound 14 in Table I (5 g) was dissolved in 30 ml of anhydrous propanol and introduced into a reactor. This solution was heated to 110° C. and 5.5 g of dimethylaminodimethoxymethane was added. The reaction mixture was maintained at 110° C. and agitated for 32 hours at atmospheric pressure. The resulting reaction mixture was then evaporated to remove the solvent and triturated with 100 ml petroleum ether, after which it was dried to provide 3.5 g of product.

It is to be understood that any of the corresponding fluoride, chloride to iodide phosphonium salts of compound 1 or any such salts of compounds 2 through 21 can be substituted in the above preparation C to provide the corresponding halogen-containing phenoxy styrylamino triphenyl phosphonium halide.

D. PREPARATION OF COMPOUND 24 OF TABLE I

The above Compound 23 (22 g) was introduced into a reactor wherein it was contacted with 165 ml of a 2 normal aqueous solution of hydrochloric acid at a temperature of 60° C. under atmospheric pressure for a period of 0.75 hour. The resulting product was then recovered by extraction with 200 ml of chloroform at room temperature and the chloroform vaporized by vacuum evaporation. The product is then triturated with petroleum ether to yield 10 g of product of over 95% purity.

It is to be understood that any of the corresponding fluoride, chloride or iodide phosphonium salts of the halogen-containing phenoxy styryl amino phosphonium bromides described in preparation C can be substituted in the above Preparation D to provide the corresponding aldehyde of the phosphonium salt.

E. PREPARATION OF COMPOUND 25 OF TABLE I

The above compound 24 (5 g) was dissolved in methanol (25 ml) and passed through a column of amberlite anion exchange resin (8.5 g of CG-4B, 200–400 mesh). After eluting the column with a further 20 ml of methanol the combined effluent was evaporated to dryness and the resulting oil triturated with cyclohexane (50 ml) and petroleum ether (50 ml) to yield 3 g of product.

It is to be understood that any of the corresponding fluoride, chloride or iodide phosphonium salts of the halogen-containing aldehyde described in preparation D can be substituted in the above preparation E to provide the corresponding dehydrohalogenated compound.

The compounds of the present invention can be applied alone as herbicides and plant growth regulants or can be employed in combination with an adjuvant in either liquid or solid form. The compositions containing the herbicides and plant growth regulants of the present invention are prepared by admixing one or more of the present herbicides or plant growth regulants with the adjuvant including diluents, extenders, carriers or conditioning agents to provide compositions in the form of finely-divded particulate solids, granules, pellets, wetable powders, dusts, or solutions and aqueous dispersions or emulsions. The concentration of the active agent in the carrier is preferably between about 5 and about 50 weight percent. Illustrative of the granular solid carriers and extenders which may be employed include the talcs, clays, diatomaceous earth, silica, pumice, sulphur, wallnut or coconut flour, wood dust, tobacco dust, charcoal and the like. Illustrative of the liquid carriers and extenders are water, propyleneglycol, N-methylpyrrolidone, benzene, xylene, cyclohexane and other liquid paraffins, acetone, methylethylketone, ethylketone, and other known extenders and carriers which may be employed singly or in combination.

The formulations may also include a minor amount up to 5% of a surfactant which includes wetting agents, dispersing agents, suspending agents, and emulsifying agents. Typical of this group are the polyoxyethylene derivatives of fatty acid esters, imidazolines, etc. It is also to be understood that the formulations of the present invention may include other biocidally active components. Such combinations are beneficial in providing herbicides or plant growth regulants of broader spectrum. For example, formulations containing equal portions of the present compound or compounds with Phosphon, Nitrofen, Ethephon or Triacontanol can be beneficial in achieving additional plant growth regulating effects.

In selecting the appropriate rate of application of the present herbicides and plant growth regulants it should be understood that the precise rates will be somewhat dependent upon the mode of application, such as soil incorporation, and pre-emergent or post-emergent plant treatment and follar dusting or drench. Generally, for herbicidal effects, the present compound is applied in amounts of from about 0.05 to about 25 pounds per acre, or more. Preferably, applications of from about 1 to about 12 pounds per acre of active ingredient is employed. The concentration of the present compound either employed alone or in a formulation is between about 0.05 ppm and about 10,000 ppm, preferably between about 1 ppm and about 500 ppm, per plant, or an effective dosage for at least 80% plant response for the effect desired.

Having thus generally described the invention, reference is now had to the accompanying examples which serve to illustrate preferred and specific embodiments, but which are not to be construed as unduly limiting to the scope of the present invention as defined in the foregoing specification and in the appended claims. In the following examples, all amounts are by weight unless otherwise indicated. It is to be understood, that any of the foregoing herbicides of this invention, as defined in Formula I and/or Formula II or listed in Table I which are not exemplified in the following examples, can be substituted therein to provide the herbicidal and/or plant growth regulating benefits of the present invention.

EXAMPLES 1–7

The herbicidal activity of the compounds listed in Table III was tested on various species of noxious weeds, namely Morning Glory, Mustard, Foxtail Millet, Japanese Millet, Crabgrass and Pigweed.

Seven 24-plant groups (i.e. 4 plants for each of the above weeds for each of the compounds tested) were grown to 3 week-old plants under sterile conditions. Aqueous solutions containing the test compound were prepared. Each group of weed was then sprayed with each of the test compound solutions at a rate of 10 lbs./acre.

Another seven 24-plant groups (i.e. 4 plants for each of the above weeds for each of the compounds tested) were grown to 3 week-old plants under sterile conditions. Again, aqueous solutions containing the test compound were prepared and the plants in replicates of 4 were sprayed to drench with each of the test compound solutions. Spraying was effected at a rate of 5 Lbs./acre.

The plants were observed 12 to 21 days after spraying and the average results reported in Table III. In Table III the test compound numbers correspond to the numbers assigned to the specific compounds shown in Table I.

TABLE III

| | | POSTEMERGENT HERBICIDAL ACTIVITY | | | | | | | | | | | |
|---|---|---|---|---|---|---|---|---|---|---|---|---|---|
| | Test Com- | % Kill | | | | | | | | | | | |
| Example No. | Compound No. | Morning Glory | | Mustard | | Foxtail Millet | | Japanese Millet | | Crabgrass | | Pigweed | |
| | | 10 lb/a. | 5 lb/a. | 10 lb/a. | 5 lb/a. | 10 lb/a. | 5 lb/a. | 10 lb/a. | 5 lb/a. | 10 lb/a. | 5 lb/a. | 10 lb/a. | 5 lb/a. |
| 1 | 1 | 40 | 0 | 80 | 0 | 5 | 0 | 20 | 0 | 80 | 0 | 100 | 0 |
| 2 | 4 | 30 | 20 | 40 | 30 | 60 | 30 | 40 | 20 | 80 | 20 | 90 | 40 |

TABLE III-continued

| | | POSTEMERGENT HERBICIDAL ACTIVITY % Kill | | | | | | | | | | | |
|---|---|---|---|---|---|---|---|---|---|---|---|---|---|
| | Test Com- | Morning Glory | | Mustard | | Foxtail Millet | | Japanese Millet | | Crabgrass | | Pigweed | |
| Example No. | pound No. | 10 lb/a. | 5 lb/a. | 10 lb/a. | 5 lb/a. | 10 lb/a. | 5 lb/a. | 10 lb/a. | 5 lb/a. | 10 lb/a. | 5 lb/a. | 10 lb/a. | 5 lb/a. |
| 3 | 5 | 30 | 20 | 0 | 20 | 80 | 30 | 20 | 30 | 70 | 20 | 100 | 0 |
| 4 | 8 | 50 | 40 | 60 | 30 | 80 | 50 | 30 | 40 | 70 | 1 | 100 | 0 |
| 5 | 18 | 30 | 30 | 60 | 30 | 80 | 50 | 20 | 20 | 50 | 40 | 100 | 90 |
| 6 | 20 | 20 | — | 90 | — | 20 | — | 10 | — | 20 | — | 40 | — |
| 7 | Phosphon | 70 | 10 | 80 | 0 | 80 | — | 30 | 0 | 80 | 20 | 100 | 90 |

EXAMPLES 8-11

The activity of the compounds listed in Table IV were tested for plant growth response in the promotion of growth retardation of soybean.

Each test compound at a concentration of 25 mg in 2 g lanoline paste was applied as a band around the stems of a group of 3 soybean plants of the Corsoy variety at the one week growth stage. The results were observed 7 days after the application and were recorded as the average length of the internodes for the group of 3 plants. The results are presented as a percentage of the control in the following Table IV.

TABLE IV

| Example No. | Test Compound No. | Internode Length (cms.) | % of Control |
|---|---|---|---|
| 8 | 7 | 2.4 | 55 |
| 9 | 12 | 2.3 | 52 |
| 10 | 19 | 3.1 | 70 |
| 11 | Phosphon | 1.0 | 23 |
| 12 | Control | 4.4 | 100 |

What is claimed is:

1. A plant growth inhibiting composition comprising an inert carrier and an inhibitor, said inhibitor consisting essentially of a compound having the formula:

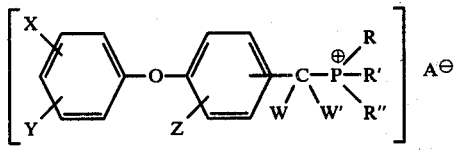

wherein $A^{\ominus}$ is a halogen anion; X, Y and Z are each independently hydrogen, a halogen atom or haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is hydrogen, —CHO or —CHN(R''')$_2$ where each R''' is independently hydrogen or alkyl of from 1 to 4 carbon atoms, optionally substituted with halogen; and W' is hydrogen or represents a bond forming a double bond between C and W when W is —CHN(R''')$_2$ an inert carrier therefor.

2. The composition of claim 1 wherein R, R' and R" are phenyl radicals; X is hydrogen and Y is a substituent other than hydrogen.

3. The composition of claim 1 wherein said inhibitor has the formula:

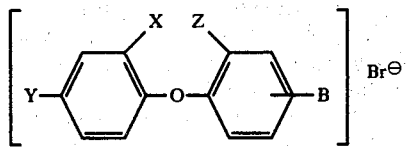

wherein X is hydrogen or chlorine; Y is hydrogen or trifluoromethyl; Z is hydrogen or, when X and Y are hydrogen, then Z is chlorine; and B is —CH$_2$P$^{\oplus}$(R)$_3$ where R is ethyl, butyl or phenyl.

4. The plant growth inhibiting composition of claim 1 containing at least one of the inhibitors therein and wherein W and W' of the inhibitor are hydrogen.

5. The plant growth inhibiting composition of claim 4 wherein R, R' and R" of the inhibitor are ethyl, butyl or phenyl.

6. The composition of claim 4 containing the inhibitor having the formula:

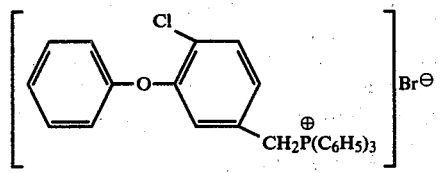

7. The composition of claim 4 containing the inhibitor having the formula:

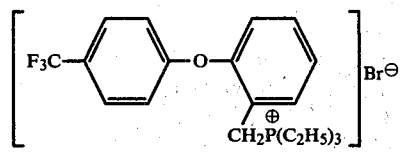

8. The composition of claim 4 containing the inhibitor having the formula:

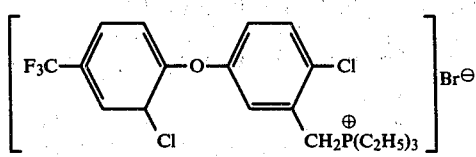

9. The composition of claim 4 containing the inhibitor having the formula:

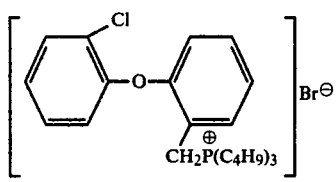

10. The composition of claim 4 containing the inhibitor having the formula:

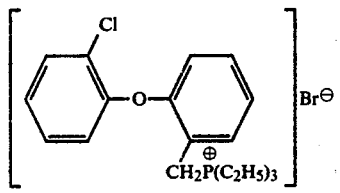

11. The composition of claim 4 containing the inhibitor having the formula:

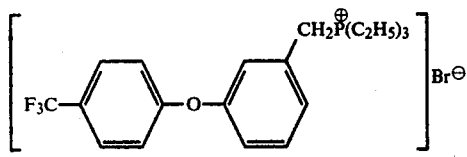

12. The composition of claim 4 containing the inhibitor having the formula:

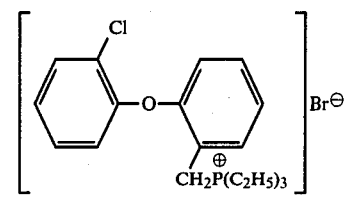

13. The process of controlling the growth of a plant by applying thereto at least a growth inhibiting amount of the composition of claim 4.

14. The process of controlling the growth of a plant by applying thereto at least a growth inhibiting amount of the composition of claim 1.

15. The process of claim 13 where in said composition the inhibitor is mixed with an inert carrier in a concentration of between about 0.08 ppm and about 10,000 ppm to provide a formulation which is applied to the plant.

16. The Process of claim 15 wherein the formulation is applied to the plant at a rate of between about 0.05 and about 25 lbs./acre.

17. The process of claim 15 where in said composition the inhibitor is mixed with a carrier in a concentration of between about 1 ppm and about 500 ppm and is applied to the plant at a rate of between about 1 and about 12 lbs./acre.

18. The process of claim 15 wherein the inhibitor in the composition is P, P, P-triphenyl-2-(2'-chlorophenoxy)-benzylphosphonium bromide.

19. The process of claim 15 wherein the inhibitor in the composition is P, P, P-triphenyl-3-(4'-trifluoromethylphenoxy)-benzylphosphonium bromide.

20. The process of claim 15 wherein the inhibitor in the composition is P, P, P-triethyl-3-(4'-trifluoromethyl-2'-chlorophenoxy) benzylphosphonium bromide.

21. The process of claim 15 wherein the inhibitor in the composition is P, P, P-tributyl-2-(2'-chlorophenoxy) benzylphosphonium bromide.

* * * * *